United States Patent
Kim et al.

(10) Patent No.: US 9,433,595 B2
(45) Date of Patent: Sep. 6, 2016

(54) PHYTOESTROGENIC COMPOSITIONS FOR PREVENTING OR TREATING SYMPTOMS ASSOCIATED WITH MENOPAUSE

(75) Inventors: Jae-Soo Kim, Goyang-si (KR); Bo-Yeon Kwak, Yongin-si (KR); Kwontaek Yi, Gimpo-si (KR); Jaekyoung Lee, Seoul (KR)

(73) Assignee: Natural Endotech Co., Ltd., Seoul (KR)

( * ) Notice: Subject to any disclaimer, the term of this patent is extended or adjusted under 35 U.S.C. 154(b) by 322 days.

(21) Appl. No.: 13/139,674

(22) PCT Filed: Dec. 26, 2008

(86) PCT No.: PCT/KR2008/007697
§ 371 (c)(1),
(2), (4) Date: Jun. 14, 2011

(87) PCT Pub. No.: WO2010/074361
PCT Pub. Date: Jul. 1, 2010

(65) Prior Publication Data
US 2011/0251145 A1    Oct. 13, 2011

(51) Int. Cl.
| | |
|---|---|
| A61K 31/192 | (2006.01) |
| A61K 31/7048 | (2006.01) |
| A61P 5/24 | (2006.01) |
| A61K 31/185 | (2006.01) |
| A23L 1/30 | (2006.01) |
| A61K 31/195 | (2006.01) |

(52) U.S. Cl.
CPC ............ *A61K 31/185* (2013.01); *A23L 1/30* (2013.01); *A61K 31/192* (2013.01); *A61K 31/195* (2013.01); *A61K 31/7048* (2013.01)

(58) Field of Classification Search
CPC .... A23L 1/30; A61K 32/185; A61K 31/192; A61K 31/195; A61K 31/7048; A61K 2300/00

USPC ..................................................... 514/27, 570
See application file for complete search history.

(56) References Cited

U.S. PATENT DOCUMENTS

| | | | | |
|---|---|---|---|---|
| 5,874,084 | A * | 2/1999 | Yng-Wong | 424/740 |
| 6,391,308 | B1 * | 5/2002 | Empie et al. | 424/757 |
| 6,569,468 | B2 * | 5/2003 | Xiao | 424/739 |
| 6,660,283 | B2 * | 12/2003 | Breton et al. | 424/401 |

FOREIGN PATENT DOCUMENTS

| | | |
|---|---|---|
| KR | 10-2008-0093203 | 10/2008 |
| WO | WO 03/080087 A1 | 10/2003 |

OTHER PUBLICATIONS

Croatto, P, naturalproductsinsider.com, Aug. 27, 2007, pp. 1-7.*
The Merck Manual, 1992, pp. 1793-1795.*
Aldrich Handbook of Fine Chemicals, 2003-2004, p. 492, entry # 13,376-0.*
Kristan et al., "Cinnamates and Cinnamamides Inhibit Fungal 17β-Hydroxysteriod Dehydrogenase," Mol. Cell Endocrinology 248:239-241, 2006.
International Search Report from International Application No. PCT/KR2008/007697, dated Sep. 17, 2009 (date of completion of search) and Sep. 18, 2009 (date of mailing of report), pp. 1-3.

* cited by examiner

*Primary Examiner* — Ganapathy Krishnan
(74) *Attorney, Agent, or Firm* — Clark & Elbing LLP; Susan M. Michaud

(57) ABSTRACT

The present invention relates to a pharmaceutical composition for preventing or treating a menopausal symptom, comprising cinnamic acid, shanzhiside methylester or a mixture thereof as an active ingredient. The composition of the present invention exhibits an excellent estrogenic activity, and is effectively utilized for treating or preventing diverse menopausal symptoms generated by estrogen deficiency during perimenopause, menopause and postmenopause.

19 Claims, 1 Drawing Sheet

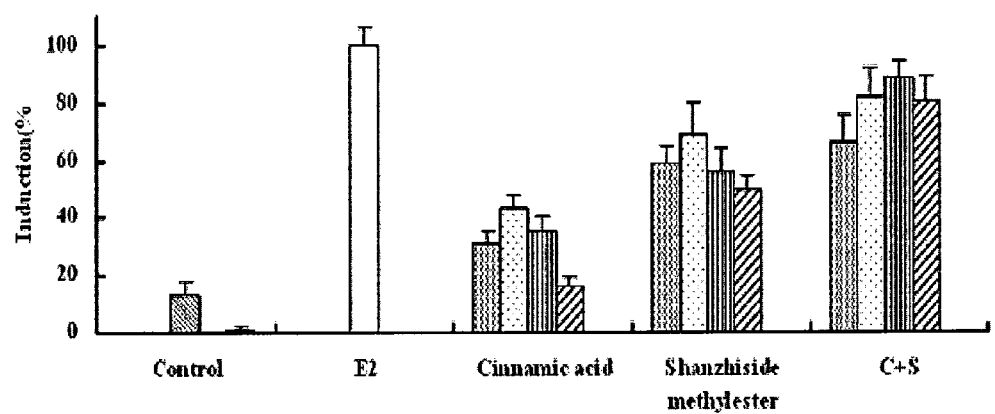

PHYTOESTROGENIC COMPOSITIONS FOR PREVENTING OR TREATING SYMPTOMS ASSOCIATED WITH MENOPAUSE

CROSS-REFERNCE TO RELATED APPLICATIONS

This application is the U.S national stage filing under 35 U.S.C §371 of international application PCT/KR2008/007697, filed Dec. 26, 2008.

BACKGROUND OF THE INVENTION

1. Field of the Invention

The present invention relates to a phytoestrogenic composition for preventing or treating symptoms associated with menopause.

2. Background of Technique

A hormone secreted from follicles in ovaries, estrogen, develops sexual organs and makes them functional to exhibit the secondary sexual character and accelerate the development of uterus, the growth of endometrium, the development of mammary gland and regular menstruation. In addition to ovaries, estrogen is secreted from placenta, adrenal cortex and testis in a small amount. Three types of steroids, estrone, estradiol and estriol found in body are known.

Estrogen is produced from androgenic precursors through an enzymatic process, aromatization. 17 beta-estradiol (E2), the most potent estrogen, which exists predominantly in premenopausal women is synthesized during the formation of ovarian follicles, is secreted into blood stream and bound to sex hormone binding globulin in a portion, and then circulates to cells in the body. The main metabolic pathway of estradiol is to be oxidized reversibly to estrone (E1), a weaker estrogen and finally converted to estriol (E3). Estrone is also produced by aromatization of androstenedione, a precursor of androgen, in the peripheral tissue. The above compounds are metabolized to form sulfate and glucuronide and excreted (Lievertz RW. Pharmacology and pharmacokinetics of estrogen. *Am J Obstet Gynecol* 156: 1289-1293 (1987)). As aromatization occurs in adipose tissue, those who have many adipose tissues have more estrogen. Estradiol and estrone may be metabolized in liver to estriol, very weak estrogen (Anderson F. Kinetics and pharmacology of estrogens in pre- and postmenopausal women. *Int J Fertil* 38 (suppl 1): 53-64 (1993)). Other estrogen metabolites as well as estradiol and estrone could function like estrogen. Therefore, it could be understood that the systematic estrogen effects in women depends on both estrogen and its metabolites.

The peak concentrations of estradiol and estrone are 200-400 pg/ml and 170-200 pg/ml in late follicular phase and decrease to the minimum concentration of 40-60 pg/ml in common during the early follicular phase.

The ratio of estradiol to estrone before menopause is generally lager than 1 (Odonnell M B. Pharmacokinetic and pharmacologic variation between different estrogen products. *J Clin Pharmacol* 35 (suppl): 18S-24S (1995)). After menopause, estrone produced by conversion of adrenal androstenedione becomes the predominant estrogen.

The metabolic pathway including 2-hydroxylation is more complicated and results in the formation of catecholesterogens. This pathway is more important in the central nervous system such as brain than in the peripheral tissue. Estrogen exhibits its effects by modifying catecholamine metabolism (Lievertz R W. Pharmacology and pharmacokinetics of estrogen. *Am J Obstet Gynecol* 156: 1289-1293 (1987)). Since catecholamine interacts with dophamin (a precursor of adrenalin) receptor, alpha 1-adrenalin receptor and serotonin receptor, it is considered to be important. Furthermore, the hydroxy derivatives of estrogen play other roles. For example, 4-hydroxy estrogen has estrogenic activity while 2-hydroxy estrogen does not. However, the 2-hydroxy derivatives of estradiol have not only estrogenic but also catecholaminergic activity (Lievertz R W. Pharmacology and pharmacokinetics of estrogen. *Am J Obstet Gynecol* 156: 1289-1293 (1987)). This accounts partially for the mechanism by which estrogens have an effect on the central nervous system.

The main physiological function of estrogen is to regulate the growth, differentiation and function of many reproductive tissues including mammary gland, uterus and ovary (Kuiper G G J M, Carlsson B, Grandien K, et al. Comparison of the ligand binding specificity and transcript tissue distribution of estrogen receptors alpha and beta. *Endocrinology* 138: 863-870 (1997)). Estrogen stimulates the growth of endometrium, myometrium, vagina and urethral epithelium. In addition, estrogen enhances vascular flow in the genital tract, increases secretion of cervical gland, and induces the expression of progesterone and luteinzing hormone receptors. Estrogen has an effect on the growth and development of backbone, fat distribution in women in addition to developing the female reproductive organs and secondary sex characteristics at puberty. Estrogen plays roles in skin, collagen tissue, neuron and cardiovascular system.

Estrogen deficiency brings up the symptoms such as hot flashes caused by vasomotor instability and in the long term, urogenital atrophy, osteoporosis, tooth loss, arteriosclerosis and coronary heart disease, and potentially, increases the risk of dementia (Maddox R W, Carson D S, Barnes C L. Estrogens and postmenopausal women. *U S Pharmacist* 23: 141-150 (1998); and Guyton A C, Hall J E. Textbook of Medical Physiology. 9th ed. Philadelphia: W.B. Saunders, 1996).

After menopause, when ovarian function declines, women experience a state of estrogen deficiency causing various menopausal symptoms such as facial flushing, depression, etc. Hormone replacement therapy is recommended for some women to alleviate menopausal symptoms of estrogen deficiency and to minimize the potential long-term health consequences of estrogen deficiency.

Administering estrogen into postmenopausal women improves vasomotion and urogenital diseases, protects and controls osteoporosis and reduces the risk of coronary heart disease (Maddox R W, Carson D S, Barnes C L. Estrogens and postmenopausal women. *US Pharmacist* 23: 141-150 (1998)).

However, the problem is that such a hormone replacement therapy may increase the activity of cancer-inducing gene, leading to increased incidence rate of cancers such as breast cancer and endometrial cancer.

The known estrogen-replacing agents are artificially synthesized or available from natural source. For example, Premarin is made from pregnant horse's urine with the increased concentration of estradiol and estrone up to that in secretion phase (Stumpf P G. Pharmacokinetics of estrogen. *Obstet Gynecol* 75 (suppl): 9S-14S (1990)). However, it has been reported during several decades that the estrogen replacement therapy results in serious side effects. A multi-center randomized double-blind clinical test (Women's Health Initiative (WHI)) would be planned with some 16,000 postmenopausal women for 8 years, but was terminated earlier in 5 years due to serious adverse events. In result, FDA forced all the HRT products to have black warning label in 2003. According to WHI, HRT increased the number of cases with breast cancer by 26%, heart disease by 29%, and stroke by 44%. Blood clot rates were more than twice as high as in those getting HRT (Journal of the American Medical Association, July 2002). NAMS (North America Menopause Society) strongly recommends that "the use of hormone combination therapy has to be prohibited for primary or secondary prophylaxis of cardiovascular diseases" and "it is not desirable to use the only estrogen therapy unless firm research data are deduced".

On the other hand, such plants as soy bean, date palm and pomegranate contain non-steroid plant compounds, phytoestrogen. Natural phytoestrogen originated from these plant functions as agonists and/or antagonist (Barrett J. Phytoestrogens: friends or foes? *Environ Health Perspect* 104: 478-482 (1996)).

Additionally, 17 beta-estradiol, estrone, estrogen sulfate are the examples of chemically modified estrogen. Such synthesized estrogen is used generally as an oral contraceptive, but hardly in hormone replacement therapy.

In short, the amount of estrogen secreted decreases with aging and the pattern of estrogen secretion is directly related to the advancement of aging. It has been recognized in the art that the administration of hormone replacement therapy allows to improve the usual symptoms of menopause, while the conventional hormone replacement therapy gives rise to severe adverse effects.

Throughout this application, various publications and patents are referred and citations are provided in parentheses. The disclosure of these publications and patents in their entities are hereby incorporated by references into this application in order to fully describe this invention and the state of the art to which this invention pertains.

DETAILED DESCRIPTION OF THE INVENTION

The present inventors have made intensive studies to develop a novel phytoestrogenic compound as an active ingredient by analyzing an estrogenic activity of various natural compounds. As results, we have discovered that cinnamic acid and shanzhiside methylester have a phytoestrogenic activity capable of effectively inducing estrogen-specific ALP (alkaline phosphatase) compared with other natural compounds.

Accordingly, object of this invention is to provide a pharmaceutical composition for preventing or treating a menopausal symptom.

It is another object of this invention to provide a food composition for preventing or treating a menopausal symptom.

It is still another object to this invention to provide a method for preventing or treating a menopausal symptom.

Other objects and advantages of the present invention will become apparent from the following detailed description together with the appended claims and drawings.

In one aspect of this invention, there is provided a pharmaceutical composition for preventing or treating a menopausal symptom, comprising: (a) a therapeutically effective amount of cinnamic acid, shanzhiside methylester or a mixture thereof; and (b) a pharmaceutically acceptable carrier.

In another aspect of this invention, there is provided a food composition for preventing or treating a menopausal symptom, comprising cinnamic acid, shanzhiside methylester or a mixture thereof as an active ingredient.

In still another aspect of this invention, there is provided a method for preventing or treating a menopausal symptom, comprising administrating to a subject the pharmaceutical composition of the present invention.

In still another aspect of this invention, there is provided a method for preventing or treating a menopausal symptom, comprising administrating to a subject the food composition of the present invention.

The present inventors have made intensive studies to develop a novel phytoestrogenic compound as an active ingredient by analyzing an estrogenic activity of various natural compounds. As results, we have discovered that cinnamic acid and shanzhiside methylester have a phytoestrogenic activity capable of effectively inducing estrogen-specific ALP (alkaline phosphatase) compared with other natural compounds.

Cinnamic acid screened as a therapeutic agent of menopausal symptoms by the present inventors may be represented by the following formula I:

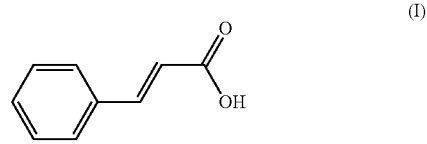 [SMILES: O=C(O)/C=C/c1ccccc1]

Cinnamic acid is a white crystalline acid, and has a melting point of 133° C. and a boiling point of 300° C. According to the conventional techniques known to those ordinarily skilled in the art, cinnamic acid has been used in flavours, synthetic indigo, and certain pharmaceuticals.

According to the present invention, cinnamic acid may be obtained from chemically synthetic products or natural substances. For example, cinnamic acid may be applied to the present invention by isolation from natural substances such as cinnamon oil, balsam, Shea butter and *Cynanchum wilfordii*.

In addition, cinnamic acid may be biosynthetically produced by action of the enzyme phenylalanine ammonia-lyase (PAL) on phenylalanine.

Shanzhiside methylester as another active ingredient of the present invention may be represented by the following formula II:

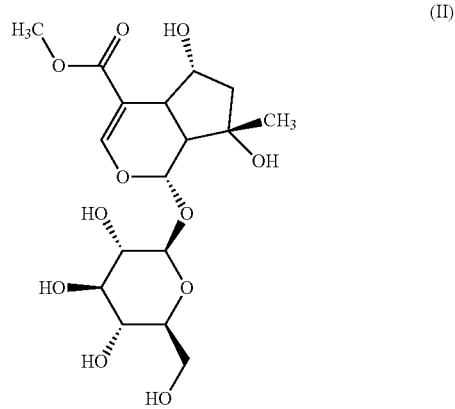

Shanzhiside methylester is a natural compound in the class of iridoid glycosides, and is known to treat mammals for hepatotoxicity, stress and immuno-deficiency (WO 2003/080087).

According to the present invention, shanzhiside methylester may be obtained from chemically synthetic products or natural materials. For example, shanzhiside methylester may be applied to the present invention by isolation from natural substances such as *Mussaenda pubescens, Phlom/s spin/dens, Lamium purpureum, Phlomlis umbrosa* and *Scoparia ericacea*.

Cinnamic acid and shanzhiside methylester used as the active ingredient in the present invention exhibit more excellent estrogenic activity than the conventional estrogen-replacing agents.

According to a preferable embodiment, the composition includes the mixture of cinnamic acid and shanzhiside methylester. As demonstrated in the below Examples, the mixture of cinnamic acid and shanzhiside methylester have synergistic estrogenic activities compared with individual substances.

The composition of this invention may be provided as a pharmaceutical composition. The pharmaceutical composition of this invention includes a pharmaceutically acceptable carrier besides the active ingredient compound. The pharmaceutically acceptable carrier contained in the pharmaceutical composition of the present invention, which is commonly used in pharmaceutical formulations, but not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered orally or parenterally, and preferably, administered orally.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition.

The term "pharmaceutically effective amount" refers to an amount enough to show and accomplish efficacies and activities of the compound of this invention as described above. Preferably, cinnamic acid and shanzhiside methylester contained as the active ingredient in the pharmaceutical composition of the present invention may be administered with a daily dosage of 0.001-10000 mg/kg (body weight).

According to the conventional techniques known to those skilled in the art, the pharmaceutical composition according to the present invention may be formulated with pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an elixir, a powder, a granule, a tablet and a capsule, and may further comprise a dispersion agent or a stabilizer.

The composition of the present invention may be provided as a food composition. In addition to cinnamic acid and shanzhiside methylester as active ingredients, the food composition of the present invention may be formulated in a wide variety of forms, for example, including proteins, carbohydrates, fatty acids, nutrients, seasoning agents and flavoring agents. For instance, natural carbohydrate may include conventional sugars such as monosaccharides (e.g., glucose, fructose, etc.); disaccharides (e.g., maltose, sucrose, oligosaccharides, etc.); and polysaccharides (e.g., dextrin, cyclodextrin, etc.); and sugar alcohols (e.g., xylitol, sorbitol, erythritol, etc.). The formulation of flavoring agent may use natural flavoring agents [thaumatin, steviai extract (e.g., rebaudioside A, glycyrrhizin), etc.]and synthetic flavoring agents (e.g., saccharine, aspartame, etc.).

Where the food composition is in the form of drinking agent, it may further include citric acid, liquid fructose, sugar, sucrose, nitric acid, malic acid, fruit juice, ulmoides extract, jujube extract, licorice extract, and so forth.

The composition of the present invention including one or more compounds of cinnamic acid and shanzhiside methylester may be highly effective in alleviation of diverse symptoms associated with menopause. The term "symptoms associated with menopause" refers to all symptoms induced by estrogen deficiency during perimenopause, menopause and postmenopause. The perimenopause is a period before practical menopause begins. During perimenopause, the production of estrogen is irregular, and the pregnancy of women is greatly diminished. The perimenopause may persist in several months or years. In addition, climacteric symptoms may be appeared in perimenopause.

The menopausal symptoms include climacteric symptoms such as sexual pain disorder, vaginal dryness, sleep disorder, mental awareness problem, arthralgia, musculoskeletal disease, indigestion, urinary incontinence, fatigue, hot flashes caused from vasomotor instability, facial flushing, night sweats, palpitations, depression, anxiety and irritability. Furthermore, serious disorders or conditions caused by insufficiency of estrogen may include osteoporosis, diseases of the genitourinary system, cardiovascular diseases, tooth loss and skin collagen loss.

The features and advantages of the present invention will be summarized as follows:

(a) The composition of the present invention includes natural substance-derived compounds, cinnamic acid or shanzhiside methylester, as an active ingredient, and exhibits an excellent estrogenic activity.

(b) The composition of the present invention may be effectively utilized for treating or preventing diverse menopausal symptoms during perimenopause, menopause, and postmenopause.

BRIEF DESCRIPTION OF THE DRAWINGS

FIG. 1 represents a histogram which analyzes estrogen-specific ALP-inducing activity. Control, E2 and C+S represent a negative control, a group treated with 17 β-estradiol and a group treated with the mixture of cinnamic acid and shanzhiside methylester with a weight ratio of 1:1, respectively. Control is negative control, and individual bars in substance-treated graph represents the samples with concentration of 5 μmol, 20 μmol, 50 μmol and 100 μmol from the left-side bar, respectively.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Preparation of Samples

Cinnamic acid was purchased from Sigma-Aldrich (USA), and shanzhiside methylester was obtained from Chemos GmbH (Germany). Each experimental group 1, group 2 and group 3 represents cinnamic acid, shanzhiside methylester and the mixture of cinnamic acid and shanzhiside with a weight ratio of 1:1.

Example 2

Analysis of Estrogenic Activity

To verify the effect of the compound of the present invention, non-reproductive tract target tissue response was carried out for measuring estrogenecity. In more detail, it was known that the induction of ALP (alkaline phosphatase) is increased and decreased in osteoblast cell, SaOS-2, by estrogen and anti-estrogen (Nasu, M., Sugimoto, T., Kaji, H. and Chihara, K. (2000) Estrogen modulates osteoblast proliferation and function regulated by parathyroid hormone in osteoblastic SaOS-2 cells: role of insulin-like growth factor (IGF)-1 and IGF-binding protein-5. *J. Endocrinol*, 167, 305-313), and in particular, the formation of mineralized bone nodules is enhanced by intermittent estrogen treatment (Rao, L. G., Liu, L. J., Murray, T. M., McDemott, E. and Zhang, X. (2003) Estrogen added intermittently, but not continuously, stimulates differentiation and bone formation in SaOS-2 cells. *Biol. Pharm, Bull*. 26(7), 936-945).

In this regard, the estrogenic activity of the compounds of the experimental groups as described above in the Example 1 was analyzed using SaOS-2 cells in this study.

For experiments, SaOS-2 cell line was purchased from Korean Type Culture Collection (KTCC). Using DMEM-high glucose/F12 supplement medium (Gibco, Carlsbad, USA) supplemented with 10% FBS (fetal bovine serum) and 1% penicillin-streptomycin, SaOS-2 cells were cultured in T-75 cm$^2$ cell flask at 37° C. under 5% $CO_2$ and 95% air condition. To determine the extent that estrogen-specific ALP is induced, SaOS-2 cells were seeded into 96-well plate at a density of 3×10$^4$ cells/well, and cultured for 24 hrs. Afterwards, the medium without phenol red was changed with a fresh medium supplemented with 1% penicillin-streptomycin, 1% sodium pyruvate, 1% NEAA (non-essential amino acids, Hyclone, USA) and 10% chachol-dextran stript FBS (CDFBS, Hyclone, USA), and cultured for 48 hrs after treatment with 1 nM17 β-estradiol (E2, Sigma-Aldrich, USA) and cinnamic acid, Shanzhiside methylester and the mixture thereof with different concentrations (5 µmol, 20 µmol, 50 µmol and 100 µmol), respectively. Thereafter, 50 µl of cell lysis buffer (100 mM Tris, 100 mM NaCl, 1 mM EDTA) was added to the culture media of each well and then, 150 µl of 30 mM p-nitrophenyl phosphate (Merk, Germany) was thoroughly mixed with shaking, followed by measuring the absorbance at 405 nm for 10 min at an interval of 50 sec. ALP induction was calculated as follows: % induction=[(Slope$_{sample}$)/(Slope$_{17\beta\text{-}estradiol}$)]×100.

The induction effect of ALP in SaOS-2 cells by cinnamic acid, shanzhiside methylester and the mixture thereof is represented in FIG. 1. In FIG. 1, control is negative control, and individual bars in substance-treated graph represent the samples with concentrations of 5 µmol, 20 µmol, 50 µmol and 100 µmol from the left-side bar, respectively.

Each substance exhibits ALP-inducing effects, and the mixture of cinnamic acid and shanzhiside methylester had more excellent effect on the induction of ALP than individual substances. Taken together, it could be appreciated that cinnamic acid and shanzhiside methylester represent remarkable estrogenic activity, and furthermore the mixture thereof exhibits a synergistic effect compared with individual substances.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

Belchetz P E. Hormonal treatment of postmenopausal women. *N Engl J Med*, 14:1062-1071 (1994).

Greendale G A, Lee N P, Arriola E R. The menopause. *Lancet*, 353(9152): 571-80 (1999).

Bungay G T, Vessey M P, McPherson C K. Study of symptoms in middle life with special reference to the menopause. *Br Med J*, 19: 181-3 (1980).

Herrington D M, Reboussin D M, Brosnihan K B, Sharp P C, Shumaker S S, Snyder T E, et al. Effects of estrogen replacement on the progression of coronary artery atherosclerosis. *N Engl J Med*, 343: 522-529 (2000).

Lien L L, Lien E J. Hormone therapy and phytoestrogen. *J Clin Pharm Ther*, 21: 101-11 (1996).

Brzezinski A, Alercreutz H, Shaoul R. Short term effects of phytoestrogen-rich diet on postmenopausal women. *Menopause*, 4: 89-94 (1997).

Elfituri A, Sherif F, Elmahaishi M, Chrystyn H. Two hormone replacement therapy (HRT) regimens for middle-eastern postmenopausal women. *Maturitas., In press,* 2005.

Edgar D, Staren O, Shuab O. Hormone replacement therapy in postmenopausal women. *The American Journal of Surgery*, 188: 136-49 (2004).

What is claimed is:

1. A method for alleviating one or more symptoms of menopause which comprises administering to a woman suffering from one or more menopausal symptoms induced by estrogen deficiency, and selected from the group consisting of sexual pain disorder, vaginal dryness, sleep disorder, mental awareness problem, arthralgia, osteoporosis, indigestion, urinary incontinence, fatigue, hot flashes caused from vasomotor instability, facial flushing, night sweat, palpitations, depression, anxiety, and irritability, a pharmaceutical composition having phytoestrogenic activity and consisting of: (a) a therapeutically effective amount of cinnamic acid, in combination with a therapeutically effective amount of shanzhiside methylester; and (b) a pharmaceutically acceptable carrier.

2. A method for alleviating one or more symptoms of menopause, which comprises administering to a woman suffering from one or more menopausal symptoms induced by estrogen deficiency, and selected from the group consisting of sexual pain disorder, vaginal dryness, sleep disorder, mental awareness problem, arthralgia, osteoporosis, indigestion, urinary incontinence, fatigue, hot flashes caused from vasomotor instability, facial flushing, night sweat, palpitations, depression, anxiety, and irritability, a food composition having phytoestrogenic activity and consisting of: (a) a therapeutically effective amount of cinnamic acid in combination with a therapeutically effective amount of shanzhiside methylester; and (b) a food.

3. The method of claim 1, wherein said menopausal symptom is selected from the group consisting of sexual pain disorder and vaginal dryness.

4. The method of claim 1, wherein said menopausal symptom is selected from the group consisting of sleep disorder and mental awareness problem.

5. The method of claim 1, wherein said menopausal symptom is selected from the group consisting of arthralgia and osteoporosis.

6. The method of claim 1, wherein said menopausal symptom is selected from the group consisting of indigestion and urinary incontinence.

7. The method of claim 1, wherein said menopausal symptom is selected from the group consisting of fatigue and hot flashes caused from vasomotor instability.

8. The method of claim 1, wherein said menopausal symptom is selected from the group consisting of facial flushing and night sweat.

9. The method of claim 1, wherein said menopausal symptom is selected from the group consisting of palpitations and depression.

10. The method of claim 1, wherein said menopausal symptom is selected from the group consisting of anxiety and irritability.

11. The method of claim 2, wherein said menopausal symptom is selected from the group consisting of sexual pain disorder and vaginal dryness.

12. The method of claim 2, wherein said menopausal symptom is selected from the group consisting of sleep disorder and mental awareness problem.

13. The method of claim 2, wherein said menopausal symptom is selected from the group consisting of arthralgia and osteoporosis.

14. The method of claim 2, wherein said menopausal symptom is selected from the group consisting of indigestion and urinary incontinence.

15. The method of claim 2, wherein said menopausal symptom is selected from the group consisting of fatigue and hot flashes caused from vasomotor instability.

16. The method of claim 2, wherein said menopausal symptom is selected from the group consisting of facial flushing and night sweat.

17. The method of claim 2, wherein said menopausal symptom is selected from the group consisting of palpitations and depression.

18. The method of claim 2, wherein said menopausal symptom is selected from the group consisting of anxiety and irritability.

19. The method of claim 2, wherein said food comprises an ingredient selected from the group consisting of a protein, a carbohydrate, a fatty acid, a nutrient, a seasoning agent, a flavoring agent and a mixture thereof.

* * * * *